United States Patent [19]

Yu et al.

[11] Patent Number: 4,532,078
[45] Date of Patent: Jul. 30, 1985

[54] REDUCTANT PRECURSOR FOR TELLURIUM IMAGING COMPOSITIONS

[75] Inventors: Terry T. Yu, Mt. Clemens; Mei-Rong Yen, Troy, both of Mich.

[73] Assignee: Energy Conversion Devices, Inc., Troy, Mich.

[21] Appl. No.: 599,949

[22] Filed: Apr. 13, 1984

Related U.S. Application Data

[62] Division of Ser. No. 392,586, Jun. 28, 1982, Pat. No. 4,446,224.

[51] Int. Cl.$^3$ .................. C07C 50/12; C07C 50/16
[52] U.S. Cl. ...................... 260/396 R; 430/346
[58] Field of Search ...................... 260/396 R

[56] References Cited

U.S. PATENT DOCUMENTS

| | | | |
|---|---|---|---|
| 4,066,460 | 1/1978 | Chang et al. | 430/495 |
| 4,106,939 | 8/1978 | Chang et al. | 430/495 |
| 4,142,896 | 3/1979 | Chang et al. | 430/495 |
| 4,195,998 | 4/1980 | Adin et al. | 430/156 |
| 4,201,588 | 5/1980 | Adin et al. | 430/167 |
| 4,281,058 | 7/1981 | Ovshinsky et al. | 430/495 |

FOREIGN PATENT DOCUMENTS 53645  5/1978  Japan .................. 260/396 R

Primary Examiner—Glennon H. Hollrah
Assistant Examiner—Raymond Covington
Attorney, Agent, or Firm—Jenner & Block

[57] ABSTRACT

Imaging films and film-forming compositions are provided which include a reducible tellurium compound, a reductant precursor, a source of labile hydrogen incorporated in a matrix. The reductant precursors are of the formulae

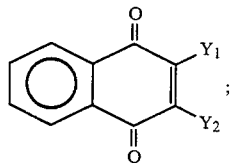

;

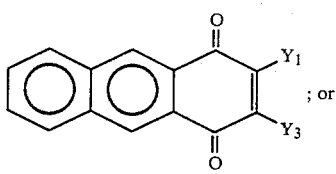

; or

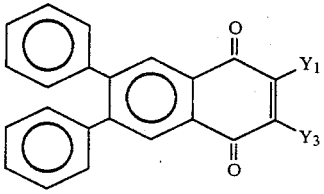

where $Y_1$ is alkoxy, $Y_2$ is chloro or alkoxy and $Y_3$ is hydrogen, chloro or alkoxy.

Methods are provided for synthesizing the reductant precursors.

2 Claims, No Drawings

REDUCTANT PRECURSOR FOR TELLURIUM IMAGING COMPOSITIONS

This is a division of application Ser. No. 392,586 filed June 28, 1982 now U.S. Pat. No. 4,446,224.

THE PRIOR ART BACKGROUND

Various methods are known for producing images or duplicates of images. The imaging materials used are, in certain cases, particular organic compounds. Some of these heretofore known methods employ mixtures of inorganic compounds such as silver halide with one or more particular types of organic compounds as sensitizers.

A new photographic process using tellurium compounds to provide the image is disclosed in U.S. patent application Ser. No. 596,646 filed July 17, 1975 (now U.S. Pat. No. 4,142,896). In accordance with U.S. Pat. No. 4,142,896, an emulsion is formed using certain reducible tellurium compounds in combination with a reductant precursor in a binder or matrix suitable for forming a film-like coating on a substrate. The film prepared therefrom is exposed image-wise to activating energy and is thereafter developed as is known in the art hereinafter described. Heat development is preferred.

Some tellurium compounds described for use in the photographic process of U.S. Pat. No. 4,142,896 may be represented, for example, by the formula $$R_x\text{—Te—}X_y \quad (1)$$

in which R is an organic radical containing at least one carbonyl group, X is halogen, preferably chlorine, and x is 1, 2 or 3, and $x+y=4$. The organic radical R may be either two independent radicals or may be joined together to form a cyclic compound. Another group of compounds mentioned in U.S. Pat. No. 4,142,896 are organic tellurium compounds which may be considered or characterized as tellurium tetrahalide adducts of ethylenic or acetylenic hydrocarbons. Some of such compounds can be represented by the formulae

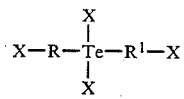  (2)

and $$(X\text{—R})_n\text{—Te—}X_n \quad (3)$$

wherein R and R$^1$ are each the residue of an ethylenic hydrocarbon and X is a halogen, preferably chlorine.

Another category of photosensitive tellurium compounds which have been found useful are halogenated tellurium compounds, such as compounds of the formula $$\text{TeCl}_n\text{Br}_m \quad (4)$$

where n is an integer from 2 to 4, and $n+m=4$. The use of such halogenated tellurium compounds in imaging processes is disclosed in U.S. Pat. No. 4,066,460 to Chang et al.

Still another category of useful tellurium compounds are described in U.S. Pat. No. 4,106,939. These compounds are tellurium tetrahalide adducts of aromatic amines in which nitrogen attached directly or indirectly to the aromatic ring is substituted by alkyls of 1–4 carbon atoms, the adduct being free of diazo groups.

The tellurium compounds such as the foregoing may be employed in conjunction with a reductant-precursor which serves as a sensitizer. The reductant-precursor is a compound which, under the influence of activating energy, will absorb radiation energy and abstract labile hydrogen from an appropriate hydrogen donor to become a strong reducing agent. The strong reducing agent reduces the tellurium compound to a divalent tellurium compound or to elemental tellurium. In either event, a change in optical density occurs which results in an imaging suitable for recording information. In general terms, the foregoing reaction may be represented by the following mechanism:

$$PQ \xrightarrow{h\nu} {}^1PQ \longrightarrow {}^3PQ$$

$$^3PQ + 2RH \longrightarrow PQ\cdot H_2 + R\text{—}R$$

$$(R^1)_2\cdot Te\cdot X_2 + 2PQ\cdot H_2 \longrightarrow 2PQ + 2R^1H=Te + 2HX$$

wherein PQ is the reductant precursor sensitizing agent; $^1PQ$ is the first excited singlet state thereof; $^3PQ$ is the triplet state thereof; RH is the hydrogen donor; $PQ\cdot H_2$ is the reductant precursor in its reduced state; and $(R^1)_2\cdot Te\cdot X_2$ is the reducible tellurium image-forming compound.

In this connection, it should be noted that the hydrogen donor need not be specifically provided, although a variety of alcohols can be used if desired. In the absence of a specially-provided hydrogen donor, the labile hydrogen can sometimes be abstracted from the organic resins used as binders. In other cases, the sensitizer can be its own hydrogen donor, and this is known to be the case with at least one sensitizer, namely, isopropoxynaphthoquinone.

A modification of the tellurium photographic process is described in Belgian Patent No. 854,193, wherein certain diols of the formula $$R_{10}\text{—CHOH—Z—CHOH—}R_{11} \quad (5)$$

may be employed as the hydrogen donor for use in conjunction with the photosensitizer described above. In the foregoing formula, $R_{10}$ and $R_{11}$ represent hydrogen and various organic substituents. Z may be a direct carbon-carbon linkage between the two hydroxy substituted carbon atoms, or may be any of various linking groups. Reference is made to Belgian Patent No. 854,193 for a fuller description of the diols referred to. In the Belgian patent, these diols are said to serve as hydrogen donors. Subsequent research has suggested that this is not completely accurate. In fact, a major portion of the diol appears to form a complex with the tellurium compound.

This finding has led to the discovery of diols of the general formula $$R\text{—O—}CH_2CHOH\text{—}CH_2OH \quad (6)$$

which have improved characteristics when used in tellurium-based photographic films.

The radical R may be a simple aliphatic group (for example, alkyl or alkenyl). Alternatively, the radical R may contain a carbonyl group (for example, an acyl radical). Preferably, however, the radical R is aromatic. Best results are obtained where the aromatic ring is separated from the ether oxygen by one methylene grouping. A more complete description of these diols is contained in U.S. patent application Ser. No. 73,700, filed Sept. 10, 1979, now U.S. Pat. No. 4,281,058, and references made thereto for additional descriptions thereof.

Still another modification in the use of tellurium compounds as photosensitive agents involves what is known as a "masked reducing agent". A number of compounds are known, such as phenidone, which will reduce organo-tellurium compounds. The reducing capacity of such compounds may be "masked"—i.e., inhibited—by appropriate substitution. In such cases, if the substituent is one which can be cleaved by the reaction products liberated upon the photoreduction of the tellurium compound, the masked reducing agent can be used to amplify the photoresponse through the mechanism Light + Sensitizer ⟶ Photoactive Reducing Agent Photoactive Reducing Agent + Tellurium Compound ⟶

Tellurium + By-Products

By-Products + Masked Reducing Agent ⟶

Demasked Reducing Agent

Demasked Reducing Agent + Tellurium Compound ⟶

Tellurium + By-Products

Since the organo-tellurium compounds commonly used release hydrogen halides (particularly hydrogen chlorides) as by-products of the reduction reaction, and the reducing agents, such as phenidone, are amino compounds, the masking agents most effectively employed are compounds which will convert the amino nitrogen into an amide. A typical masked reducing agent thus is the compound

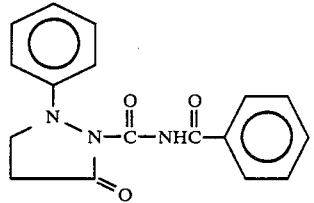
(7)

A more complete description of masked reducing agents may be found in Belgian Pat. No. 863,052 of July 19, 1978, and reference thereto is made for additional descriptions thereof.

As an alternative to the masked reducing agents described in Belgian Pat. No. 863,052, a new class of masked reducing agents may be substituted, represented by the general formulae $$R^1—NY—NY_2;$$ (8)

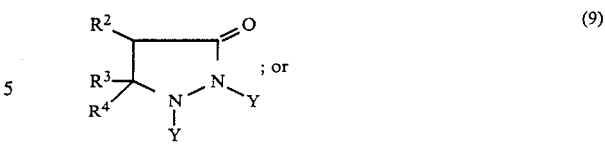

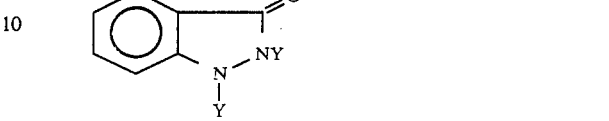

wherein Y is hydrogen or

said compound containing at least one

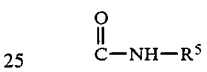

group. In the foregoing formulae, $R^1$ may be alkyl, alkanoyl, alkoxycarbonyl, phenyl, benzyl, benzoyl, nitrophenyl, benzylcarbonyl, phenylmethyl, phenylethyl or phenylpropylcarbonyl, or aminocarbonyl. $R^2$, $R^3$ and $R^4$ each, and independently, may be hydrogen, alkyl or phenyl and amino. $R^4$ may be phenyl, nitrophenyl, halophenyl, alkyl, mono-, di- or tri-haloalkyl, benzoyl, alkylphenyl, or alkylcyanophenyl. The masking group may be substituted at either one or both of the amino hydrogen sites of the reducing agent. The alkyl groups referred to above may contain up to seven carbon atoms. Such compounds are conveniently accessible through reaction of the parent hydrazine or pyrazoline with an isocyanate of the formula $$R^5—N=C=O$$ (11)

A more complete description of these masked reducing agents is found in U.S. patent application Ser. No. 277,720, filed June 26, 1981 now U.S. Pat. No. 4,340,662 and reference thereto is made for additional descriptions thereof.

In practice, the foregoing ingredients, i.e., a tellurium derivative, a reductant precursor sensitizer, and additional ingredients such as the glycol and masked reducing agent, are combined in a suitable matrix to form an emulsion which may be spread into a film on an appropriate carrier or substrate. A latent image in the film is formed by exposure to imaging energy, for example, a light image.

After formation of the latent image, a visible image is developed by heating the exposed film as described in U.S. Pat. No. 4,142,896.

The speed or light sensitivity of the film is determined by the amount of energy necessary to produce an image. For many applications it is desirable to have an imaging film that is relatively fast, and in addition, has a low optical density relative to the optical density of the image formed by the film. It is also desirable for the film to be sensitive to light in the visible spectrum facilitating use of the film in many practical applications. The organo-tellurium imaging system previously described generally did not possess the characteristics of sensitivity to visible light while at the same time having good speed, such as less than about 30,000 ergs of imaging energy per square centimeter to achieve an optical density of one greater than fog.

SUMMARY OF THE INVENTION

The present invention concerns an improvement in the above described organo-tellurium system for photosensitive emulsions. In accordance with the invention, organo-tellurium imaging systems are provided which have excellent speed (generally less than about 30,000 ergs/cm$^2$ to achieve an optical density of one over fog) and which have excellent sensitivity to electromagnetic energy in the visible region (400–600 nanometers).

The improved spectral sensitivity is attained by the use of certain types of reductant precursors which are quinones. The quinones of the present invention may be represented by the general formulae:

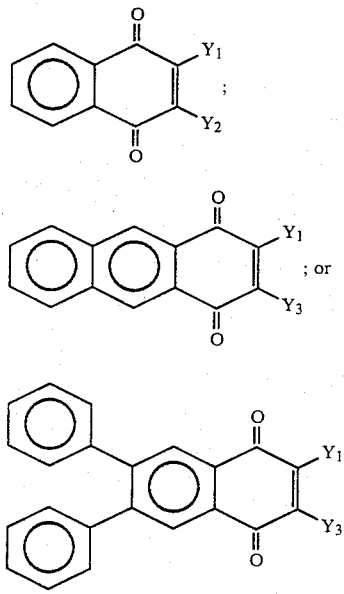

wherein $Y_1$ is alkoxy, generally having less than 6 carbon atoms, (methoxy, ethoxy, propoxy, butoxy, pentoxy, etc.), $Y_2$ is alkoxy, generally having less than 6 carbon atoms (methoxy, ethoxy, propoxy, butoxy, pentoxy, etc.) or chloro and $Y_3$ is hydrogen, chloro or alkoxy, generally having less than 6 carbon atoms (methoxy, ethoxy, propoxy, butoxy, pentoxy, etc.). Generally, best results are obtained when $Y_1$ has greater than one carbon atom. Use of the quinone compounds in accordance with the invention results in unexpected improvements in spectral sensitivity and/or speed. The film-forming compositions and films in accordance with the invention may include one or more of the foregoing quinones.

Representative quinone compounds within the scope of the invention are: 3-chloro-2-isopropoxy-1,4-naphthoquinone; 3-chloro-2-isopropoxy-1,4-anthraquinone; 3-chloro-2-isopropoxy-6,7-diphenyl-1,4-naphthoquinone; 3-chloro-2-(3'-pentoxy)-1,4-naphthoquinone; 3-chloro-2-(2'-butoxy)-1,4-naphthoquinone; 3-chloro-2-(3',3'-dimethyl-2'-butoxy)-1,4-naphthoquinone; 2,3-diisopropoxy-1,4-naphthoquinone; 3-chloro-2-methoxy-1,4-naphthoquinone; 2,3-dimethoxy-1,4-naphthoquinone; 3-chloro-2-(t-butoxy)-1,4-naphthoquinone; 3-chloro-2-ethoxy-1,4-naphthoquinone; 3-chloro-2-(n-butoxy)1,4-naphthoquinone; 3-chloro-2-(2'-methylpropoxy)-1,4-naphthoquinone; and 2-isopropoxy-1,4-anthraquinone.

The reductant precursors, when incorporated into the organo-tellurium imaging system results in imaging film having increased sensitivity to visible light at relatively high speed.

In accordance with another aspect of the present invention, the improved reductant precursors may be incorporated into imaging systems which utilize reducible organo-metallic compounds other than tellurium compounds. For example, copper, cobalt, silver, nickel and mercury are metals which may form suitable reducible compounds for imaging. However, the same speed and spectral sensitivity may not result as when used in organo-tellurium imaging systems.

DETAILED DESCRIPTION OF EMULSIONS ACCORDING TO THE PRESENT INVENTION

An emulsion formulated in accordance with the present invention contains a tellurium compound, a reductant precursor of the above description, and an appropriate matrix or binder. Optionally, other components may also be included in the emulsion. A masked reducing agent may be included, as disclosed in U.S. patent application Ser. No. 277,720 filed June 26, 1981. A diol may be included, preferably a glyceryl compound of U.S. Pat. No. 4,281,058. An alcohol may also be included, preferably when a glyceryl compound of U.S. Pat. No. 4,281,058 is included, as disclosed in copending U.S. patent application Ser. No. 392,580 filed June 28, 1982, now U.S. Pat. No. 4,446,222. Water may also be included, as disclosed in copending U.S. patent application Ser. No. 392,576 filed June 28, 1982, now U.S. Pat. No. 4,448,877. A base may be included as disclosed in copending U.S. patent application Ser. No. 392,579 filed June 28, 1982, now U.S. Pat. No. 4,451,556.

It is anticipated that reducible organo-metallic imaging compounds and other reducible metal compounds, other than tellurium compounds, may be utilized in accordance with the invention. For example, other metals which can form organo-metallic imaging compounds, include copper, silver, nickel, mercury and cobalt. For example, cobalt imaging compounds are disclosed in U.S. Pat. No. 4,201,588 to Adin et al. Specific organo metallic compounds which may be used include, for example, copper-2,4-pentanedionate, nickel-2,4-pentanedionate, mercury acetate and silver behenate.

The image-forming tellurium: A number of image-forming tellurium compounds are described in the prior art and such compounds are generally useful in the present invention. In general, the present invention contemplates using these and other tellurium compounds which undergo analogous reduction reactions in the presence of a reductant precursor as hereinafter described.

It has been found that many tellurium compounds possess certain properties which adapt them especially for use in imaging processes. In general, these are compounds from which, as a result of the imaging and developing steps generally referred to above, elemental tellurium is deposited from the tellurium compounds. Tellurium is chain-forming in character, and it is generally deposited from the tellurium compounds useful for photographic purposes (preferably including thin needles), the compounds being capable of rapid nucleation and growth as crystallites, which crystallites grow as chains and largely or mainly as needles. Such chains or needles are opaque and are characterized by excellent light scattering properties to produce good optical density observed after thermal or other development.

Effects which may involve oxide formation are substantially restricted to surface effects as distinguished from effects which cause degradation through the bodies of the needles or chains.

Preferably, the tellurium imaging compound is an organo-tellurium compound such as disclosed in U.S. Pat. No. 4,142,896 of Chang et al. These compounds are organic tellurium compounds which inherently possess sensitizer properties (and/or may be mixed with a separate sensitizer) in which the tellurium is linked directly to at least one carbon atom or the organic radical of the organo-tellurium material, the organic tellurium compound being of one structure and having a detectable characteristic which is capable of undergoing a change in response to the application of imaging energy in the form of particle or wave radiation to produce a material of different structure having another detectable characteristic. The material having a different structure and different detectable characteristics resulting from the imaging step is sometimes referred to as the "image-forming compound".

The tellurium imaging compound may be an organo-metallic compound such as disclosed in U.S. Pat. No. 4,062,685, which is hereby incorporated by reference.

A particularly advantageous subgroup of the imaging organo-tellurium compounds utilized in the practice of the present invention comprises organic compounds which contain an organo radical and halogen attached directly to the tellurium atom, there being at least one carbonyl group in the organo radical. Certain of them are adducts of tellurium halides, notably tellurium tetrachloride, with organic compounds, notably ketones or similar chromophores, containing at least one carbonyl group in the organic compound. They may, thus, be considered or characterized as organo-tellurium compounds or adducts containing halogen, namely, chlorine, bromine, iodine, and fluorine, attached directly to the tellurium atom. Most of this particular class or group of said imaging compounds have two carbonyl-containing organo radicals. Those which are especially useful in the practice of the present invention have chlorine as the halogen but, in certain cases, although generally less satisfactory, other halogens can be present. The imaging compounds should be selected to be soluble or homogeneously dispersible in any particular matrix material which may be utilized, as is described hereafter. Many of this group of imaging organo-tellurium compounds may be represented by the formula $$R_x\text{—Te—Hal}_y \quad (15)$$

where R is an organo radical containing at least one carbonyl group, Hal is halogen, especially chlorine, x is 1, 2 or 3, and $x+y=4$, subject to the proviso that Te is linked directly to carbon in an organo radical. Preferably, x is 2 or 3.

Others can be represented by the formula $$R_2\text{—Te—Hal}_4 \quad (16)$$

where R is a carbonyl-containing organic radical, and Hal is halogen.

The R radical can be aliphatic, cycloaliphatic or aromatic (mononuclear or dinuclear) or a combination thereof and may contain one or more hetero atoms in the chain or rings. It may be unsubstituted or substituted by various organic or inorganic radicals, which may assist in or at least do not interfere with the desired imaging effect, illustrative of such radicals being $C_1$-$C_6$ alkyl, corresponding oxyalkyl radicals, acetyl, nitro, $C\equiv N$, Cl, Br, F, etc. Generally speaking, the aforesaid organo-tellurium imaging compounds which contain a trihalide group as, for instance, acetophenone tellurium trichloride, tend to have relatively low melting points (about 70°–80° C.), and are more hygroscopic and less stable than those generally similar compounds containing two halogen atoms and, therefore, such trihalides are less desirable for use in the practice of the present invention.

A more limited class of this particular subgroup of imaging organo-tellurium compounds may be represented by the formula $$(\text{Ar—CO—CH}_2)_2\text{Te—Hal}_2 \quad (17)$$

where Ar is an aromatic hydrocarbon radical, which may be substituted or unsubstituted, as indicated above, and Hal is halogen, especially chlorine. This subgroup of compounds, particularly where Hal is chlorine, represents especially advantageous embodiments of the invention, with respect to the imaging organo-tellurium compounds which are used in the practice of the present invention.

Another subgroup of imaging organo-tellurium compounds, useful in the practice of and contemplated by the present invention, which do not contain a carbonyl group in an organo radical but in which tellurium is linked directly to carbon are compounds which may be considered or characterized as tellurium tetrahalide adducts of ethylenic or of acetylenic hydrocarbons. These compounds are generally conveniently produced by reacting 1 to 2 moles, particularly 2 moles, of the ethylenic or acetyleneic hydrocarbon with 1 mole of tellurium tetrahalide, especially preferred for such use being TeCl$_4$. Certain of such compounds can be represented by the formulae:

$$\begin{array}{c} \text{Hal} \\ | \\ \text{Hal—R}^2\text{—Te—R}^3\text{—Hal; and} \\ | \\ \text{Hal} \end{array} \quad (18)$$

$$(\text{Hal—R}^2)_x\text{—Te—Hal}_y \quad (19)$$

where $R^3$ and $R^2$ are each the residue of an ethylenic hydrocarbon, for instance, an alkene or a cycloalkene, Hal is chlorine, bromine or iodine, especially chlorine, x is 1 to 3, and $x+y=4$.

Illustrative of the ethylenic and acetyleneic hydrocarbons which can be adducted with tellurium tetrahalides to produce such imaging organo-tellurium compounds are propylene; butene-1; isobutylene; butene-2; 2,3-dimethyl-2-butene; 3,3-dimethyl-1-butene; 2,4-dimethyl-1-pentene; 4,4-dimethyl-1-pentene; 2,5-dimethyl-3-hexene; dipentene; 1,1-diphenylethylene; 1-heptene; 1-hexene; 2-methyl-1-hexene; 3-methyl-1-hexene; 4-methyl-1-hexene; 2-ethyl-1-hexene; 2-isopropyl-1 -hexene; 2-methyl-1-pentene; 2-methyl-2-pentene; 2-ethyl-2pentene; 3-methyl-1-pentene; piperylene;

vinylcyclohexene; vinylcyclopentene; 2-vinylnaphthalene; 1,2,4-trivinylcyclohexene; 4-methyl-1-cyclohexene; 3-methyl-1-cyclohexene; 1-methyl-1-cyclohexene; 1-methyl-1-cyclopentene; cycloheptene; cyclopentene; cyclohexene; 4,4-dimethyl-1-cyclohexene; 2-methylbutene-1; 3-methylbutene-1; and 1-octene; lower alkyl and lower alkoxy derivatives of various of the alkenes such as cyclohexene; 1-pentyne; 2-pentyne; 1-hexyne; and 3-methyl-1-butyne.

The preparation of the aforementioned organic tellurium compounds as well as many examples thereof are more fully set forth in U.S. Pat. No. 4,142,696, which is hereby incorporated by reference.

As indicated above, tetrahalides of tellurium in which the halide is at least one member selected from the group consisting of chlorine and bromine are also useful as the image-forming material in the present invention. Such tellurium halides are fully described in U.S. Pat. No. 4,066,460, the specification of which is hereby incorporated by reference. Certain of these imaging materials can be represented by the formula

$$TeCl_nBr_m \qquad (20)$$

where n is an integer from 1 to 4 and $m+n=4$. Typical tellurium tetrahalides which may be used are $TeCl_4$; $TeCl_2Br_2$; and $TeClBr_3$. $TeCl_4$ is especially useful. Reference is made to U.S. Pat. No. 4,066,460 for a fuller description of these tellurium tetrahalides and their use as image-forming compounds.

Still another group of image-forming compounds are certain compounds derived from tellurium tetrahalides which are described in U.S. Pat. No. 4,106,939 to Chang et al. These involved compounds are adducts of tellurium tetrahalide with aromatic amines exemplified by the tellurium tetrachloride adduct of dimethylaniline, which adduct is free of diazo groups. More specifically, these tellurium tetrahalide adducts are formed by combining a tellurium tetrahalide with an aromatic amine in which nitrogen attached directly or indirectly to the aromatic radical is substituted by alkyls containing from 1 to 4 carbon atoms, the imaging organo-tellurium material being free from diazo groups.

These aromatic amine adducts of the tellurium tetrahalides are fully described in U.S. Pat. No. 4,106,939 to Chang et al.; the disclosure thereof is hereby incorporated by reference.

The active tellurium compounds may, if desired, be formed in situ, for example, by using a tellurium oxide or a tellurium salt in combination with a suitable organic compound. Sometimes the in situ formation is promoted by the presence of an acid. For example, bis(acetophenone) tellurium dichloride or tellurium oxide or alkali metal tellurates may be combined with one of the glycols described below to form a tellurium-organic compound complex which is active. It is believed that the reaction is analogous to the reaction between organic tellurium compounds such as described above and a diol. Preliminary information suggests that the reaction is favored by an acidic medium. Small amounts of an acid such as anhydrous hydrogen chloride may be added. Alternatively, halogen-containing tellurium compounds will provide the requisite acidity.

The reductant precursor: In addition to the tellurium image-forming compound, the imaging systems of the present invention include a reductant precursor, or sensitizer, which, as described above, is a compound that, under the influence of activating energy, has the property of extracting labile hydrogen from a hydrogen donor to become a reducing agent with respect to the image-forming tellurium compound. The activated reducing agent then reduces the tellurium compound to produce the desired image. The hydrogen donor may be an external source of hydrogen such as an alcohol specifically provided for the purpose. However, the hydrogen donor may equally well be an appropriate group which is a part of the molecular structure of the reductant precursor.

Preferred reductant precursors include: 3-chloro-2-isopropoxy-1,4-naphthoquinone; 3-chloro-2-isopropoxy-1,4-anthraquinone; 3-chloro-2-isopropoxy-6,7-diphenyl-1,4-naphthoquinone; 3-chloro-2-(3'-pentoxy)-1,4-naphthoquinone; 3-chloro-2-(2'-butoxy)-1,4-naphthoquinone; 3-chloro-2-(3', 3'-dimethyl-2'-butoxy)-1,4-naphthoquinone; 2,3-diisopropoxy-1,4-naphthoquinone; 3-chloro-2-methoxy-1,4-naphthoquinone; 2,3-dimethoxy-1,4-naphthoquinone; 3-chloro-2-(t-butoxy)-1,4-naphthoquinone; 3-chloro-2-ethoxy-1,4-naphthoquinone; 3-chloro-2-(n-butoxy)1,4-naphthoquinone; 3-chloro-2-(2'-methylpropoxy)-1,4-naphthoquinone; and 2-isopropoxy-1,4-anthraquinone.

It will be understood that not all reductant precursors will be effective or equally effective, with each given imaging material, even taking into account the utilization of imaging energy in the sensitivity range of the reductant precursor employed and that suitable selections of combinations of particular imaging materials and particular reductant precursors will be required to be made for achieving desirable or optimum results. Such selections, however, can be made relatively readily.

In general, in connection with the foregoing matters, it may be noted that reductant precursors have $\eta \pi^*$ states, both singlet and triplet, of lower energies than $\pi$, $\pi^*$ states and, at least in most cases, compounds which have their $\pi$, $\pi^*$ states of lowest energy will not be photosensitively effective, although, in certain limited cases, compounds which fulfill the test of having lower energy $\eta \rightarrow \pi^*$ than $\pi \rightarrow \pi^*$ transitions do not function as reductant precursors. However, the above consideration is, in the main, an effective one for determining in advance whether a given compound will function as a reductant precursor for use in the practice of the present invention. In any event, a simple preliminary empirical test in any given instance can readily be carried out if necessary by preparing a test emulsion using the desired imaging compound and reductant precursor.

Preparation of the Reductant Precursors: Preparation of the reductant precursors in accordance with the invention is now described. Generally, to form the naphthoquinones or anthraquinones in accordance with the invention, a suitable starting material is reacted with a suitable alkoxide to form the desired reductant precursor.

When it is desired to form a reductant precursor of the general formula

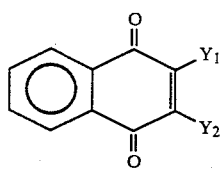

(21)

wherein $Y_1$ is alkoxy and $Y_2$ is alkoxy or Chloro, 2,3-dichloro-1,4-naphthoquinone is reacted with a metal alkoxide, such as a sodium alkoxide, the alkoxide corresponding with the desired alkoxy group. The metal alkoxide can be formed by reacting an alcohol with an active metal, such as sodium. For example, the reaction of sodium with isopropanol yields sodium isopropoxide. Thus, to prepare 2,3-diisopropoxy-1,4-naphthoquinone, sodium isopropoxide is reacted with 2,3-dichloro-1,4-naphthoquinone, preferably at room temperature, forming 2,3-diisopropoxy-1,4-naphthoquinone. 2-chloro-3-isopropoxy-1,4-naphthoquinone is prepared in a similar manner, except that the alkoxide is added slowly to a cooled (preferably 0°–5° C. or about ice bath temperature) suspension of 2,3-dichloro-1,4-naphthoquinone. In this manner, only one of the chloro groups is replaced by an isopropoxy group. Other reductant precursors in accordance with the invention having one alkoxy group and one chloro group, such as 3-chloro-2-(2'-butoxy)-1,4-naphthoquinone, 2-chloro-3-isopropoxy-1,4-anthraquinone and 2-chloro-3-isopropoxy-6,7-diphenyl-1,4-naphthoquinone, can be prepared in a similar manner. The latter two compounds would be prepared from 2,3-dichloro-1,4-anthraquinone and 2,3-dichloro-6,7-diphenyl-1,4-naphthoquinone, respectively.

If $Y_1$ and $Y_2$ are different alkoxy, one alkoxide is added slowly to replace one chloro and the product recovered and then the product is reacted in a similar manner with the other alkoxide.

Reductant precursors of the general formula

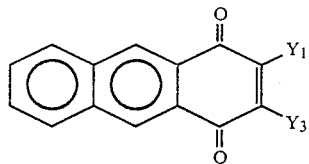

where $Y_1$ is alkoxy and $Y_3$ is hydrogen, chloro or alkoxy can be prepared by reacting 2-chloro-1,4-anthraquinone (if $Y_3$ is to be hydrogen) or 2,3-dichloro-1,4-anthraquinone (if $Y_3$ is to be chloro or alkoxy) with a suitable metal alkoxide as previously described with respect to the naphthoquinones.

Reductant precursors of the general formula

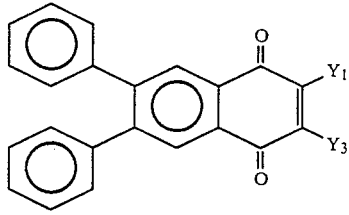

where $Y_1$ is alkoxy and $Y_3$ is hydrogen, chloro or alkoxy can be prepared by reacting 2,3-diphenylbutadiene with 2,3-dichlorobenzoquinone in acetic acid to give 2,3-dichloro-6,7-diphenyl-1,4-naphthoquinone, which is then reacted with a metal alkoxide as previously described with respect to 2,3-dichloro-1,4-naphthoquinone. Alternatively, where $Y_4$ is hydrogen, 2-chlorobenzoquinone is utilized in place of 2,3-dichlorobenzoquinone.

The Masked Reducing Agent: In accordance with the invention, a masked reducing agent is included. A typical masked reducing agent thus is the compound 1-phenyl-2-benzoylamido-3-pyrazolidinone

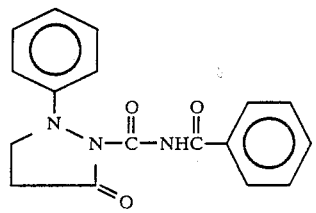

A more complete description of masked reducing agents may be found in Belgian Pat. No. 863,052 of July 19, 1978, and reference thereto is made for additional descriptions thereof.

As an alternative to the masked reducing agents described in Belgian Pat. No. 863,052, a new class of masked reducing agents may be substituted, represented by the general formulae

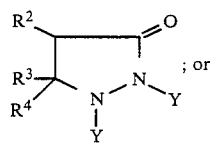

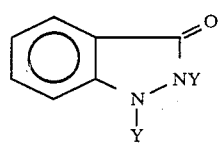

wherein Y is hydrogen or

said compound containing at least one

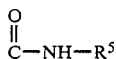

group. In the foregoing formulae, $R^1$ may be alkyl, alkanoyl, alkoxycarbonyl, phenyl, benzyl, benzoyl, nitrophenyl, benzylcarbonyl, phenylmethyl, phenylethyl or phenylpropylcarbonyl, or aminocarbonyl. $R^2$, $R^3$ and $R^4$ each, and independently, may be hydrogen, alkyl or phenyl and amino. R4 may be phenyl, nitrophenyl, halophenyl, alkyl, mono-, di- or tri-haloalkyl, benzoyl, alkylphenyl, or alkylcyanophenyl. The masking group may be substituted at either one or both of the amino hydrogen sites of the reducing agent. The alkyl groups referred to above may contain up to seven carbon atoms. Such compounds are conveniently accessible through reaction of the parent hydrazine or pyrazoline with an isocyanate of the formula

A more complete description of these masked reducing agents is found in U.S. patent application Ser. No.

277,720, filed June 26, 1981 now U.S. Pat. No. 4,340,662 which is hereby incorporated by reference.

The Base: When a masked reducing agent is utilized, a base can be included. The inclusion of a base provides the unexpected result of improving the speed (light sensitivity) and/or improving the optical density of the exposed portions after development of imaging film made with such compositions. The inclusion of a base may also reduce the background fog or optical density of unexposed portions of the film.

The base may be organic or inorganic and should be sufficiently alkaline to ionize the masked reducing agent. In general, any base which improves the performance of the film, such as, for example, increased speed, increased optical density of exposed portions or decreased fog of unexposed portions, can be utilized. Preferably, bases which produce unwanted deleterious effects will be avoided. Suitable inorganic bases include, for example, metal hydroxides and ammonium hydroxide. More specifically, alkali metal hydroxides and alkaline earth metal hydroxides can be utilized. Useful alkali metal hydroxides include those of lithium, sodium, potassium, rubidium, and cesium. Lithium hydroxide is the preferred alkali metal hydroxide. Useful alkaline earth metal hydroxides include those of magnesium, calcium and barium. The hydrated form of the metal hydroxide can be used. It is anticipated that more than one base can be included in the imaging film composition.

Alternatively, the organic base may be an amine compound or a nitrogen atom containing heterocyclic compound.

Suitable amines for use in accordance with the invention include primary, secondary and tertiary amines which may be aliphatic or aromatic. More particularly, suitable amines are those such as, for example, methylamine, dimethylamine, trimethylamine, ethylamine, diethylamine, triethylamine, n-, di-n- and tri-n- propylamine, isopropylamine, n-butylamine, isobutylamine, di-n-butylamine, tertbutylamine, and n-tetradecylamine. In general, those amines of the following formula may be suitable:

R—NH$_2$ where R is aliphatic (for example CH$_3$, C$_2$H$_5$, C$_3$H$_7$, etc.).

The R radical may be unsubstituted or substituted by various organic or inorganic radicals, which do not interfere with the desired imaging effect.

Cyclic compounds, such as pyridine and piperidine, are also suitable, and may be unsubstituted or substituted by various organic or inorganic radicals, which do not interfere with the desired imaging effect.

While not wishing to be bound by theory, it is believed that the base ionizes the masked reducing agent facilitating the formation of a complex between the ionized masked reducing agent, positive tellurium ions and the latent image formed by the reductant precursor after exposure of the film to imaging energy. The complex is believed to be very susceptible to electron transfer, facilitating formation of a visible image.

In general, alkaline earth or alkali metal hydroxides are preferred over organic bases. The metal ions from the base may form a beneficial complex with the reductant precursor which makes the reductant precursor more active.

The amount of base present in the film-forming composition is variable. Generally, there is no minimum amount of base required to provide an improved film. However, the degree of improvement is related to the amount of base present, up to a certain amount, for each particular film formulation and base. Beyond that amount, generally the photoresponse of the film diminishes. The optimum amount of a particular base for a particular formulation can easily be determined simply by formulating film-forming compositions containing various amounts of a particular base and testing the performance of the films made therefrom.

The Diol: In accordance with the present invention, there may also be included a diol which reacts with the tellurium compound to form an active intermediate complex. While the chemistry of the complex is not well understood, we believe that, in general, the complex requires approximately 2 moles of diol for each mole of tellurium. Preferably, the diol, when present, is used in excess of the minimum amount to form a complex since the diol will also function as a source of labile hydrogen to provide the source of hydrogen required in the reaction of the reductant precursor.

While the present invention involving the use of certain reductant precursors can be practiced without the inclusion of a diol, the presence of a diol is preferred especially when a masked reducing agent is present. The presence of a diol serves to markedly reduce the optical density of unexposed areas (i.e., thus increasing the contrast between the exposed and unexposed areas) particularly when a masked reducing agent is present. Thus, while masked reducing agents can be used in the absence of a diol, tellurium film compositions containing masked reducing agents tend to have a relatively high optical density in the unexposed areas because the reducing capacity of the masked reducing agent is not fully inhibited by the masking group.

One group of diols which may be used in formulating imaging compositions are diols of the formula $$\begin{array}{c} \text{H} \quad\quad \text{H} \\ | \quad\quad\quad | \\ R^4-C-Z-C-R^5 \\ | \quad\quad\quad | \\ \text{OH} \quad \text{OH} \end{array}$$

wherein each of R$^4$ and R$^5$ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents an arylene group (for example, phenylene), the group (—C≡C—), the group (—CR$^6$=CR$^7$)$_n$, wherein n represents a whole number, for example, 1 or 2, and each of R$^6$ and R$^7$ represents hydrogen or an alkyl group or taken from part of a carbocyclic or heterocyclic ring. Z also may be omitted—that is, the two hydroxy-substituted carbons are joined directly to each other. The following table illustrates a number of diols which may be used:

| No. of the Compound | R$^4$ | Z | R$^5$ | Boiling Point (BP) °C. or Melting Point (MP) °C. |
|---|---|---|---|---|
| 1 | H | — | H | BP 198 |
| 2 | 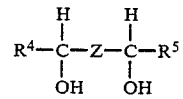 | — | H | MP 67 |
| 3 | H$_3$C— | — | H | BP 189 |
| 4 | H$_3$C— | — | —CH$_3$ | BP 183 |

-continued

| No. of the Compound | R⁴ | Z | R⁵ | Boiling Point (BP) °C. or Melting Point (MP) °C. |
|---|---|---|---|---|
| 5 | H | —C≡C— | H | MP 52–54 |
| 6 | H |  | H | MP 112 |
| 7 | HO(CH$_2$)$_4$— | — | H | BP 178/5 mm Hg |
| 8 | C$_2$H$_5$OC—<br>‖<br>O | — | C$_2$H$_5$O—C—<br>‖<br>O | BP 280 |

A fuller description of the foregoing diols may be found in Belgian Pat. No. 854,193, the disclosure of which is hereby incorporated by reference.

Preferably, however, the diol is of a more complex type than disclosed in the above-mentioned Belgian patent application. These more complex diols are the subject matter of U.S. Pat. No. 4,281,058, which is hereby incorporated by reference.

The preferred diols, as described in U.S. Pat. No. 4,281,058, are compounds of the formula

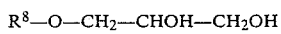

R$^8$—O—CH$_2$—CHOH—CH$_2$OH

In the foregoing compound, R$^8$ may be alkyl, acyl, thiazolinyl, alkenyl, phenyl, alkylphenyl, alkenylphenyl, hydroxyalkylphenyl, benzyl, alkylbenzyl, alkoxybenzyl, hydroxyalkylbenzyl, and halobenzyl and similar radicals.

The "thio" analogs of the foregoing compounds can be used (i.e., compounds in which the radical R$^8$ is joined to the glycerol residue by a thio linkage in place of the oxy linkage.

Preferred compounds of the foregoing structure are those in which the radical R$^8$ is benzyl or a substituted benzyl. The use of the diols of the foregoing structure has been found to be preferred since they are more effective in reducing the optical density of the unexposed areas than are the diols described in Belgian Pat. No. 854,193.

Ancillary Ingredients: In addition to the foregoing principal ingredients of the present formulation, ancillary ingredients may be included for various purposes. Thus, for example, it has been found that certain materials enhance the shelf life of unexposed virgin dry film compositions of the present invention, and in certain instances, they also enhance the sensitivity of said film compositions. Illustrative embodiments of such additional or supplemental materials, which contain ether or polyether linkages in the molecules thereof, are such materials or polymers as polyethylene- 20 sorbitan monolaurate; polyethylene-20 sorbitan monooleate; Polyox-10; Polyox-80; Polyox-750; polyethylene glycol-400 distearate; polyethylene glycol-600 distearate; poly (1,3-dioxolane); poly (tetrahydrofuran); poly (1,3-dioxepane); poly (1,3-dioxane); polyacetaldehydes; polyoxymethylenes; fatty acid esters of polyoxymethylenes; poly (cyclohexane methylene oxide); poly (4-methyl-1,3-dioxane); polyoxetanes; polyphenylene oxides; poly [3,3-bis (halomethyl) oxocyclobutane]; poly (oxypropylene) glycol epoxy resins; and copolymers of propylene oxides and styrene oxides. Such materials can be incorporated in the imaging film compositions in varying amounts, generally from 5 to 20% by weight of the solid imaging film compositions. In certain cases they enhance or prolong the shelf life or storage life, under given storage conditions, as much as 50% or even very substantially more timewise, and, as indicated, they also, in various cases, effectively increase film sensitivity.

Again, the inclusion in the imaging films of reducing sugars has been found, generally speaking, to bring about an enhancement in density of the image area (O.D. image-O.D. background), when the film is imaged as disclosed above and then developed, for instance, at about 120°–150° C. and for the order of about 15 seconds, especially where the imaging film is freshly prepared or not older than about a day after initial preparation. Such films, when exposed to imaging energy and then developed resulted in the production of a positive image (i.e., the optical density is greater in the non-exposed areas than in the exposed areas) in contrast to the negative working system which exists in the usual practice of the present invention. The inclusion of reducing sugars in the imaging compositions also enables development of the image, after exposure to imaging energy, to take place at lower temperatures, even at room temperatures, in a period of several hours, for instance, commonly in 10, 12 or 15 hours. The reducing sugars which can be employed are many, illustrative of which are dextrose, glucose, arabinose, erythrose, fructose, galactose, fucose, mannose and ribose. Especially effective are dextrose, arabinose, galactose, fucose and ribose. The reducing sugars can be used in variable amounts, but generally in equivalent amounts, or somewhat smaller or greater, in relation to the amount of imaging organo-tellurium materials in the imaging compositions.

It may be desirable in many cases to include a small amount of silicone oil or similar material as is well known to aid in coating of smooth continuous films.

Several other ancillary ingredients may be utilized, which can have the effect of increasing the sensitivity of the film and/or optical density after exposure. These ancillary ingredients include: indoaniline dyes of the general formula

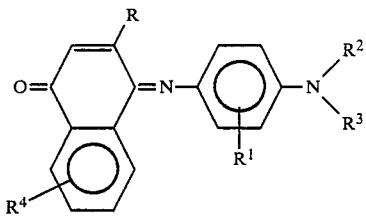

where R$^1$–R$^4$ may be, each and independently, hydrogen or alkyl (N,N-(p-dimethylaminophenyl)-1,4-naphthoquinone (indophenol blue) for example); indane-1,3-dione derivatives such as 2-phenylindane-1,3-dione; and cyanine dyes of the general formula

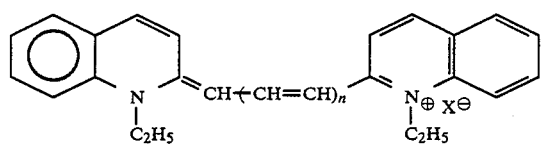

where n=1, 2 or 3 and X is chloro or iodo (1,1'-diethyl-2,2'-carbocyamine chloride (pinacyanol chloride), for example).

The matrix material: A film composition in accordance with the present invention is completed by dissolving the ingredients and optional ingredients described above in a suitable matrix. The matrix should be as concentrated as is practicable in the active ingredients, i.e., the least amount of matrix is preferably used. The amount of matrix should be sufficient as to just retain the various active ingredients in a solid solution. An additional quantity of matrix may be used, however, that obviously tends to dilute the concentration of active ingredients, thereby slowing down the photoresponse of the film composition. The selection of matrix materials, of course, must be related to the active ingredients used so as to provide the maximum solubility for any particular composition.

The matrix materials, into which the imaging organo-tellurium materials, and the separate sensitizers when employed, are incorporated to produce the imaging film or coating, are solids at room temperature, and they can be selected from a relatively large number of materials. Care should be taken to insure that the matrix material does not absorb undesired components, such as water from the atmosphere. They should desirably be at least in part of amorphous character and it is especially desirable that they be glassy, polar amorphous materials having a glass transition temperature, which desirably should not exceed about 200° C. and may be as low as about 50° C., and, better still, should be within the range of about 80°–120° C. They are generally polymeric materials. Illustrative thereof are cyanoethylated starches, celluloses and amyloses having a degree of substitution of cyanoethylation of ≧2; polyvinyl-benzophenone; polyvinylidene chloride; polyethylene terephthalate ("MYLAR"); cellulose esters and ethers such as cellulose acetate, cellulose propionate, cellulose butyrate, cellulose acetate butyrate, acetyl cellulose, methyl cellulose, ethyl cellulose, hydroxypropyl cellulose, polyvinylcarbazole; polyvinyl chloride; polyvinyl methyl ketone; polyvinyl alcohol; polyvinylpyrrolidone; polyvinyl methyl ether; copolymers of vinylidene chloride and acrylonitrile; polyvinyl acetate, polyvinyl butyral; polystyrene; polymethyl methacrylate; polyvinyl pyrrolidone; styrenebutadiene copolymers; polyamides; polyacrylic and polymethacrylic alkyl esters such as polymethyl methacrylate and polyethyl methacrylate; copolymer of polyvinyl methyl ether and maleic anhydride; various grades of polyvinyl formal resins such as so-called 12/85, 6/95E, 15/95S, 15/95E, B-79, B-98, and the like, sold under the trademark "FORMVAR"-(Monsanto Company). Of special utility is polyvinyl formal 15/95% which is a white, free flowing powder having a molecular weight in the range of 24,000–40,000 and a formal content expressed as percent polyvinyl formal of approximately 82%, possessing high thermal stability, excellent mechanical durability, and resistance to such materials as aliphatic hydrocarbons, and mineral, animal and vegetable oils. These polymeric materials or resins and their preparation are well known to the art. Also of special utility are various grades of cellulose acetate butyrate polymers sold by the Eastman Kodak Company under the trade designation "CAB", particularly "CAB 500-5".

In addition to their functioning as carriers for and holding together in a unitary composition the imaging organo-tellurium materials, sensitizers and any other ingredients which may be incorporated into the imaging film or coating or layer and their functioning as dry or essentially dry film-forming materials to provide thin films and providing mechanical durability in the finished imaged film, at least many of them appear also to play a chemical or physical role in the imaging process by providing, importantly, a source of readily easily abstractable hydrogen and, thus, appear to play a significant role in the latent image formation mechanism, as discussed hereafter. In certain instances, it may be desirable to decrease the viscosity of the matrix, which can be done, by way of illustration, by the addition of certain plasticizers, for instance, dibutylphthalate or diphenylphthalate, which additions tend to result in the production of images desirably of higher optical densities but which, however, also tend to have the disadvantage of increasing background fogging.

It may be noted that matrix materials of the type which contain basic groups may complex with the imaging organotellurium materials and, therefore, to the extent that such complexing may occur, the use of such matrix materials should be avoided.

Water: The compositions may also include water. A small quantity of water, generally added to the matrix material, prior to combination with the other film-forming components, serves to improve the speed of the film. However, too much water may cause a tellurium oxide to be precipitated when the components of the film-forming composition are combined, and this should be avoided. For a more complete description of the inclusion of water, reference is made to U.S. patent application Ser. No. 392,576, filed June 28, 1982 now U.S. Pat. No. 4,448,877.

Alcohol: The compositions of the invention may also include an alcohol. Preferably, the alcohol will be utilized when a diol as previously described is present in the composition. The alcohol and diol may form a complex with the tellurium compound, providing a film having enhanced speed and/or improved background fog. The alcohol may be primary, secondary or tertiary. Primary monohydric alcohols are preferred, such as n-butanol and n-propanol, for example. For a more complete description of the inclusion of an alcohol, reference is made to U.S. patent application Ser. No. 392,580, filed June 28, 1982 now U.S. Pat. No. 4,446,224.

Formulation of Film Compositions: In the production of the films or thin layers of the imaging material compositions, which are generally prepared in the form of solutions or homogeneous dispersions and coated or laid down on a substrate, it is especially desirable to dissolve or homogeneously disperse the ingredients in an organic solvent. Illustrative of suitable solvents are methyl ethyl ketone (MEK), dimethylformamide (DMF), chloroform, tetrahydrofuran (THF), dimethylacetamide (DMA), dioxane, dichloromethane and ethylene dichloride, or compatible mixtures of such organic solvents or with other organic solvents. A particularly useful solvent is a 50:50 mixture of dichloromethane and methyl ethyl ketone. After the solution or homogeneous dispersion is filmed on a substrate in any suitable manner, the major proportions of such organic solvent or solvents are evaporated off, preferably at a relatively low temperature and, sometimes desirably, under subatmospheric pressures or in vacuo, until the film or coating is substantially dry to the touch, such dry-to-the-touch coating being especially desirable for handling and processing purposes. Although such films or coatings may be, generally speaking, dry to the touch, it should be understood that this does not mean that the film is free from organic solvent. Indeed, it has been found that it is frequently very desirable that the finished films or coatings, prior to exposure to imaging energy, contain a small percentage, commonly of the general order of about 2 to 3%, by weight of the film or coating, or organic solvent, for instance, dimethylformamide (DMF) since its presence appears to play a favorable role in the sensitivity of the system in relation to the latent image formation and/or ultimate image obtained after the development step. The elimination of all or essentially all of the DMF, or other organic solvent or solvents, from the virgin film prior to the imaging and development frequently leads to a decrease in sensitivity. In any event, in any given instance where drying of the virgin imaging film has been carried out to a point where essentially no organic solvent is present, and whereby sensitivity is unduly reduced, sensitivity can be increased or restored by adding a small amount of organic solvent to the film prior to exposing it to imaging energy.

The imaging film or coating thickness are variable but will usually fall within the range of about 1 to about 35 μm with about 5 to 15 μm generally being a good average. In thickness in terms of millimeters (mm), such may vary from about 0.0005 to about 0.05 mm, or much greater, such as from 0.05 to 5 mm, the selected thickness being dependent upon the particular use to which the imaging film is to be put.

The production of the imaging organo-tellurium materials, and the coating, handling and processing operations, to the extent which may be required, are carried out under appropriate light conditions, as those skilled in the art will readily understand. For instance, the formulation of the coating compositions and the coating and drying operations are conveniently carried out under amberlite filtered light (weak transmission at 550 nm). The dry film prior to imaging, is desirably stored in the dark. In certain cases, avoidance of contact of certain of the ingredients with certain metals may be in order where undesired reactions, such as reductions, may occur. In general, the vessels or containers, stirrers, etc., utilized should be made of glass or other vitreous materials or other materials inert to the coating ingredients to insure against contamination or possible undesired reactions. It is advantageous, in general, to prepare the imaging compositions shortly prior to coating them on the selected substrate. Under suitable storage conditions, which generally are conditions of darkness and reasonable avoidance of air or oxidizing atmospheres and humidity conditions, the stability of the imaging compositions is good.

In the imaging compositions, the proportions of the matrix, the imaging organo-tellurium material and the reductant precursor are variable. In those special cases where the imaging organo-tellurium material utilized is one which also inherently or concomitantly possesses desired sensitizing properties, as noted above, a separate reductant precursor is not necessary. It may, however, even in such cases, be desirable to employ a separate or added reductant precursor which may be of entirely different sensitizing properties from that inherently possessed by the particular imaging organo-tellurium material utilized. In any event, generally speaking, excluding the organic solvent or solvents, where employed as described below, at least in most cases the matrix material, which is a normally solid material, that is, solid at room temperature, will be employed in amounts in excess of any one of the other materials and will also usually be present in major amount, that is more than 50% and broadly in the range up to 90% by weight, of the total materials present in the imaging composition. The imaging organo-tellurium material, generally also a normally solid material, will ordinarily constitute from about 1 to above 20 parts per 100 parts of matrix, usually about 5-10 parts per 100 parts of matrix. The reductant precursor, which is usually a solid, will usually be employed in lesser proportions, commonly of the order of about 5 to 20%, usually about 6 to 15%, by weight, of the imaging composition, although, in certain cases the proportions thereof can be substantially higher, approximately or even exceeding somewhat the proportions of the imaging organo-tellurium material. With further regard to the proportions of the aforesaid ingredients, it may be stated that the area density of the reductant precursor is desirably selected so that about 70-95% of the photons falling on the film in the region of the absorption bands of the reductant precursor are absorbed. Considerably higher concentrations of reductant precursor would leave the dark side of the film unexposed and no advantage would thus be served. In general, for optimal results in many cases, the mole concentration of the imaging organo-tellurium material should be reasonably close to or roughly approximate to that of the reductant precursor. The concentration of the polymer matrix material should be sufficient to produce an essentially amorphous film without bringing about precipitation of the imaging organo-tellurium material, the sensitizer and other supplemental ingredients when utilized. Excess polymer matrix material also tends to decrease the sensitivity of the film.

The amount of diol should be present in a concentration sufficient to provide at least 2 moles of diol for each mole of tellurium compound, and preferably to provide up to a ratio of 6:1 moles. As indicated above, our work has suggested that a complex is formed between the diol and the tellurium compound in a molar ratio of 2:1, and that excess diol above that is useful to provide a source of labile hydrogen for reaction with the reductant precursor. Larger amounts of the diol may be used if desired. To some extent, improved results are obtained when these larger amounts of diol are used; however, there is a point of diminishing returns above which increasing the amount of diol will not provide commensurate improvement in photoresponse of the finished film.

The masked reducing agent may be present in amounts of 1% up to 200% by weight of the tellurium compounds. Measurably improved sensitivity can be found in accordance with the present invention with even very small amounts of masked reducing agent and within limitations the degree of improvement is in proportion to the amount of masked reducing agent which is incorporated in the film. Again, however, a law of diminishing returns is observed, and while large amounts of the masked reducing agent will be incorporated—in the order of 2 to 4 times the amount of tellurium compound—beyond these large amounts the increase in photoresponse obtained is not commensurate with the increased amount of masked reducing agent incorporated.

The film-forming compositions as described above will be applied to any suitable substrate. Glass, porcelain, paper and various plastic substrates have been found suitable. For the purposes of forming film-like materials, transparency is obviously desirable. For this purpose, film of polyethylene terephthalate have been found particularly suitable. Other substrates include, for example, polyimides, nylon and triacetyl cellulose.

Fixing: After exposure and development, which development may be accomplished by heating, the film may be fixed as described in U.S. Pat. No. 4,142,896. The film may also be fixed by contacting the film with an alcohol, such as isopropanol, for example. A small amount of ketone such as acetone, for example, may also be included with the alcohol. Especially useful is a solution of 50 parts isopropanol/1 part acetone (by volume).

Additional considerations which those skilled in the art in formulating and using tellurium-based film compositions may utilize are apparent from U.S. Pat. No. 4,142,896, the disclosure of which is hereby incorporated by reference.

This invention is further illustrated by the following examples:

EXAMPLE 1

A reductant precursor in accordance with the invention, 2-chloro-3-isopropoxy-1,4-naphthoquinone (CIPNQ), was prepared as hereinafter described. 3.5 grams of sodium and 100 ml of isopropanol were refluxed in 200 ml of benzene, to prepare the alkoxide, sodium isopropoxide. An additional 150 ml of benzene was added after all the sodium dissolved in order to prevent the precipitation of the alkoxide. The diluted alkoxide was then added drop-wise to a previously cooled suspension of 30 grams of 2,3-dichloro-1,4-naphthoquinone in 200 ml of benzene at 0°–5° C. The reaction was carried out under red light since the product is light sensitive. The reaction was complete within 30 minutes. The reaction mixture was then washed with water and crude product was obtained after the organic layer was dried and concentrated. Recrystallization in methanol yielded 25 grams of pure, yellow, shiny crystals of CIPNQ.

EXAMPLE 2

A reductant precursor in accordance with the invention, 2,3-diisopropoxy-1,4-naphthoquinone (DIPNQ), was prepared as hereinafter described. The alkoxide was prepared by refluxing 3 grams of sodium and 200 ml isopropanol in 200 ml benzene. After all the sodium dissolved, the alkoxide solution was added slowly to a suspension of 10 grams of 2,3-dichloro-1,4-naphthoquinone in 50 ml isopropanol at room temperature. The reaction mixture was acidified with 4 N HCl and extracted with benzene. The organic layer was dried and concentrated. The crude product thus obtained was purified by dissolving it in 100 ml of benzene and washing with several portions of 2.5% aqueous NaOH until the wash solution was colorless. 6 grams of pure dark red DIPNQ liquid was obtained after the washed benzene layer was dried, decolorized and concentrated. The decolorizing agent was Norit A ®, marketed by the J. T. Baker Chemical Company.

EXAMPLE 3

A reductant precursor in accordance with the invention, 2-isopropoxy-1,4-anthraquinone (IPAQ), was prepared as hereinafter described. 1.6 grams of 1,4-anthraquinone in 10 ml of acetic anhydride was treated with 0.8 ml of borontrifluoride etherate. The 1,4-anthraquinone went into solution slowly with a slight temperature rise (to 40° C.) and after two hours, crystals of the triacetate began to separate. After standing overnight at room temperature, the crystalline product had separated from the dark brown solution. The solid was collected and washed with methanol. The material collected was crystalline, weighing 1.34 grams without purification. The mixture was stirred with 1.0 grams of sodium methoxide in 20 ml of methanol yielding the dark red sodium salt 2-hydroxy-1,4-anthraquinone. This salt was collected and washed with methanol. Then it was dissolved in 100 ml of $H_2O$ and the solution was filtered and acidified with hydrochloric acid. The 2-hydroxy-1,4-anthraquinone collected was a light yellow powder and the yield was 0.75 grams.

4 grams of 2-hydroxy-1,4-anthraquinone synthesized as described above, 20 ml of isopropanol and 12 ml of borontrifluoride etherate were heated at 70° C. overnight, yielding the desired product, 2-isopropoxy-1,4-anthraquinone. After cooling, the solution was filtered, dried, and washed with standard $KHSO_4$. Finally, the product was washed with water and dried at room temperature overnight.

EXAMPLE 4

A reductant precursor in accordance with the invention, 2,3-dichloro-1,4-anthraquinone, was prepared as hereinafter described. A mixture of $\alpha,\alpha,\alpha',\alpha'$-tetrabromo-o-xylene (4.22 grams), sodium iodide (10.0 grams), 2,3-dichloro-1,4-benzoquinone (2.0 grams) and dry dimethylformamide (35 ml) was stirred at 80°–90° C. for 24 hours. After pouring into cold water, the iodine color was discharged by the gradual addition of aqueous sodium bisulfate. The brown precipitate was air dried overnight to yield 1.6 grams of crude 2,3-dichloro-1,4-anthraquinone.

EXAMPLE 5

A reductant precursor in accordance with the invention, 2,3-dichloro-6,7-diphenyl-1,4-naphthoquinone, was prepared as hereinafter described. 2,3-diphenylbutadiene (9 grams) and 2,3-dichlorobenzoquinone (13.8 grams) and acetic acid (100 ml) were stirred at 75° C. for 20 hours. The resulting acetic acid solution was diluted and the precipitated product collected and dissolved in chloroform (100 ml). The solution was extracted with an aqueous solution of 2N NaOH. The light yellow colored organic layer was dried over magnesium sulfate, filtered and evaporated to give the solid compound.

EXAMPLE 6

2-chloro-3-isopropoxy-1,4-anthraquinone, a reductant precursor in accordance with the invention, was prepared from 2,3-dichloro-1,4-naphthoquinone by a method similar to that described in Example 1.

EXAMPLE 7

2-chloro-3-isopropoxy-6,7-diphenyl-1,4-naphthoquinone, a reductant precursor in accordance with the invention, was prepared from 2,3-dichloro-6,7-diphenyl-1,4-naphthoquinone by a method similar to that described in Example 1.

EXAMPLES 8–22

Tellurium imaging films were made and tested, some utilizing reductant precursors not in accordance with the present invention and other films utilizing the reductant precursors of the present invention. The effectiveness of the various reductant precursors was evaluated by making identical tellurium imaging films except for the type of reductant precursor. Each film was made by combining the specific reductant precursor and amount as set forth in the following table with 0.65 grams of bis(acetophenone) tellurium dichloride (a tellurium imaging compound), 0.625 grams of a masked 1-phenyl-3-pyrazolidone of the formula

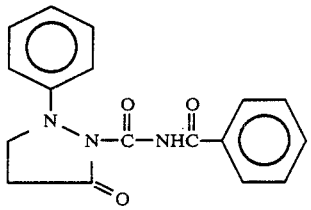

2.4 grams of ortho-methoxy benzyl glyceryl ether (a diol), 10.42 grams of CAB-500-5 (matrix) containing an additional 1.5 milliliters of water and 160 milliliters of a 50:50 mixture (by volume) of methylene dichloride and methyl ethyl ketone (solvent). The components were stirred together in complete darkness at room temperature until a homogeneous viscous solution was obtained. The solution was then coated on a MYLAR substrate at an area coverage of approximately 2 grams of bis(acetophenone) tellurium dichloride per square meter. The resulting film was heated in an oven at 50°–55° C. for three hours.

The photographic response of the film was evaluated by determining the wavelength of light at which maximum absorbtion took place and by determining the maximum wavelength of light to which the film was sensitive. The speed of the film was evaluated by determining the amount of energy required to produce an optical density of one greater than fog. The minimum and maximum optical density of the film was determined by exposing the film to imaging energy through a photographic step tablet having eleven steps and an optical density range of approximately 0.5 to 3.05. The step tablet was in contact with the film during exposure. A Honeywell Strobonar Model No. 710 Xenon flash tube was utilized to provide imaging energy, spaced approximately 10 inches from the film. After exposure, the film was developed by heating the film at a temperature of 150°–155° C. for 40–45 seconds. The maximum optical density (OD MAX) and minimum optical density or fog (OD MIN) was determined with a MacBeth Model T-P 504 Densitomer using a red filter.

The films utilizing the various reductant precursors exhibited the following results:

EXAMPLE 8

| Reductant Precursor | Results | |
|---|---|---|
| (structure: 2-isopropoxy-1,4-naphthoquinone) | Speed (@ OD of one over fog) 1,800 ergs/cm$^2$ | |
| | OD Min | 0.47 |
| | OD Max | 3.12 |
| (2-isopropoxy-1, 4-naphthoquinone) | Spectral Sensitivity | |
| | Maximum Sensitivity | 365 nm |

-continued

| Reductant Precursor | Results | |
|---|---|---|
| Amount: 300 mg | Upper Range Sensitivity | 412 nm |

EXAMPLE 9

| Reductant Precursor | Results | |
|---|---|---|
| (structure: 3-chloro-2-methoxy-1,4-naphthoquinone) | Speed (@ OD of one over fog) greater than 30,000 ergs/cm$^2$ | |
| | OD Min | 0.55 |
| | OD Max | 2.79 |
| (3-chloro-2-methoxy-1, 4-naphthoquinone) Amount: 300 mg | Spectral Sensitivity | |
| | Maximum Sensitivity @ | 435 nm |
| | Upper Range Sensitivity | 550 nm |

EXAMPLE 10

| Reductant Precursor | Results | |
|---|---|---|
| (structure: 2,3-dimethoxy-1,4-naphthoquinone) | Speed (@ OD of one over fog) greater than 30,000 ergs/cm$^2$ | |
| | OD Min | 0.21 |
| | OD Max | 1.13 |
| (2,3-dimethoxy-1, 4-naphthoquinone) Amount: 280 mg | Spectral Sensitivity | |
| | Maximum Sensitivity | 430 nm |
| | Upper Range Sensitivity | 560 nm |

EXAMPLE 11

| Reductant Precursor | Results | |
|---|---|---|
| (structure: 3-chloro-2-isopropoxy-1,4-naphthoquinone) | Speed (@ OD of one over fog) 1,900 ergs/cm$^2$ | |
| | OD Min | 0.55 |
| | OD Max | 2.79 |
| (3-chloro-2-isopropoxy-1, 4-naphthoquinone) Amount: 380 mg | Spectral Sensitivity | |
| | Maximum Sensitivity | 490 nm |
| | Upper Range Sensitivity | 550 nm |

EXAMPLE 12

| Reductant Precursor | Results | |
|---|---|---|
| (structure: 3-chloro-2-(t-butoxy)-1,4-naphthoquinone) | Speed (@ OD of one over fog) greater than 30,000 ergs/cm$^2$ | |
| | OD Min | 0.53 |
| | OD Max | 1.13 |
| (3-chloro-2-(t-butoxy)-1, 4-naphthoquinone) Amount: 400 mg | Spectral Sensitivity | |
| | Maximum Sensitivity | not determined |
| | Upper Range Sensitivity | not determined |

EXAMPLE 13

| Reductant Precursor | Results | |
|---|---|---|
| 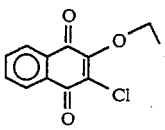 (3-chloro-2-ethoxy-1, 4-naphthoquinone) Amount: 360 mg | Speed (@ OD of one over fog) 20,000 ergs/cm$^2$ OD Min OD Max | 0.54 1.82 |
| | Spectral Sensitivity Maximum Sensitivity Upper Range Sensitivity | 460 nm 510 nm |

EXAMPLE 14

| Reductant Precursor | Results | |
|---|---|---|
| 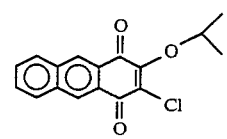 (3-chloro-2-(n-butoxy)-1, 4-naphthoquinone) Amount: 400 mg | Speed (@ OD of one over fog) 16,000 ergs/cm$^2$ OD Min OD Max | 0.51 1.95 |
| | Spectral Sensitivity Maximum Sensitivity Upper Range Sensitivity | 470 nm 510 nm |

EXAMPLE 15

| Reductant Precursor | Results | |
|---|---|---|
| 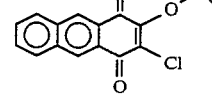 (3-chloro-2-(2'-methylpropoxy)-1, 4-naphthoquinone) Amount: 400 mg | Speed (@ OD of one over fog) 21,000 ergs/cm$^2$ OD Min OD Max | 0.57 2.02 |
| | Spectral Sensitivity Maximum Sensitivity Upper Range Sensitivity | 490 nm 510 nm |

EXAMPLE 16

| Reductant Precursor | Results | |
|---|---|---|
| 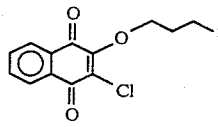 (2-isopropoxy-1, 4-anthraquinone) Amount: 300 mg | Speed (@ OD of one over fog) 4,900 ergs/cm$^2$ OD Min OD Max | 0.46 2.05 |
| | Spectral Sensitivity Maximum Sensitivity Upper Range Sensitivity | 470 nm 520 nm |

EXAMPLE 17

| Reductant Precursor | Results | |
|---|---|---|
| 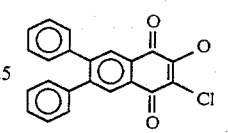 (3-chloro-2-isopropoxy-1, 4-anthraquinone) Amount: 560 mg | Speed (@ OD of one over fog) 2,600 ergs/cm$^2$ OD Min OD Max | 0.43 2.41 |
| | Spectral Sensitivity Maximum Sensitivity Upper Range Sensitivity | 480 nm 610 nm |

EXAMPLE 18

| Reductant Precursor | Results | |
|---|---|---|
| 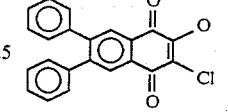 (3-chloro-2-isopropoxy-6,7-diphenyl-1, 4-naphthoquinone) Amount: 300 mg | Speed (@ OD of one over fog) 8,200 ergs/cm$^2$ OD Min OD Max | 0.47 1.83 |
| | Spectral Sensitivity Maximum Sensitivity Upper Range Sensitivity | 510 nm 580 nm |

EXAMPLE 19

| Reductant Precursor | Results | |
|---|---|---|
| 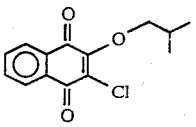 (3-chloro-2-(3'-pentoxy)-1, 4-naphthoquinone) Amount: 420 mg | Speed (@ OD of one over fog) 2,170 ergs/cm$^2$ OD Min OD Max | 0.50 2.43 |
| | Spectral Sensitivity Maximum Sensitivity Upper Range Sensitivity | 490 nm 550 nm |

EXAMPLE 20

| Reductant Precursor | Results | |
|---|---|---|
| 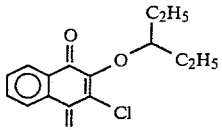 (3-chloro-2-(2'-butoxy)-1, 4-naphthoquinone) Amount: 420 mg | Speed (@ OD of one over fog) 2,330 ergs/cm$^2$ OD Min OD Max | 0.47 2.31 |
| | Spectral Sensitivity Maximum Sensitivity Upper Range Sensitivity | 490 nm 550 nm |

EXAMPLE 21

| Reductant Precursor | Resuls | |
|---|---|---|
| 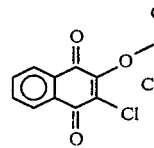 (3-chloro-2-(3',3'-dimethyl-2'-butoxy)-1,4-naphthoquinone) Amount: 470 mg | Speed (@ OD of one over fog) 2,510 ergs/cm$^2$ OD Min OD Max | 0.56 2.56 |
| | Spectral Sensitivity | |
| | Maximum Sensitivity | 490 nm |
| | Upper Range Sensitivity | 550 nm |

EXAMPLE 22

| Reductant Precursor | Results | |
|---|---|---|
| 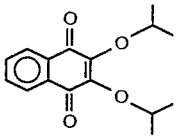 (2,3-diisopropoxy-1,4-naphthoquinone) Amount: 210 mg | Speed (@ OD of one over fog) 1,460 ergs/cm$^2$ OD Min OD Max | 0.47 2.60 |
| | Spectral Sensitivity | |
| | Maximum Sensitivity | 510 nm |
| | Upper Range Sensitivity | 580 nm |

While the invention has been described with respect to preferred embodiments, it is to be understood that the invention is capable of numerous rearrangements, modifications and changes which will be apparent to one skilled in the art and it is intended that the invention encompass such rearrangements, modifications and changes which fall within the scope of the appended claims.

We claim:
1. The compound 2,3-diisopropoxy-1,4-naphthoquinone.
2. The compound 2-isopropoxy-1,4-anthraquinone.

* * * * *